United States Patent [19]

McColley

[11] Plant 4,090

[45] Aug. 9, 1977

[54] DISTINCT VARIETY OF PHILODENDRON PLANT

[76] Inventor: Robert H. McColley, P.O. Box 17126, Orlando, Fla. 32810

[21] Appl. No.: 729,583

[22] Filed: Oct. 4, 1976

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

There is disclosed herein, a Philodendron plant ("King of Spades") particularly characterized by the contrasting red and green colors of the leaves in both immature and mature state, some of the outstanding characteristics being the hastate leaf shape which gives a more open look to the whole plant while being more compact and having a higher gloss to the leaves, the glossy bronze red color of the sheath covering as the leaf opens, the dark red sheath thereafter curling back and hanging on to the stem for long periods of time, together with superior disease resistance to bacterial soft rot and shot-gun fungus.

1 Drawing Figure

DESCRIPTION OF THE INVENTION

The instant invention relates to a new and distinct variety of Philodendron plant which I designate "King of Spades" and which was hybridized by me in the vicinity of Orlando, Fla.

The seedling hereof is the result of an extensive breeding program which I carry on, and is actually the result of an inbreeding program which I have conducted using a variety which I developed and which I designate as "Burgundy" being well-known in the trade.

Since this program involved many crosses and selections of which no specific record has been kept, I nevertheless selected the instant plant for the reasons which are set forth hereinafter.

Asexual reproduction of my new variety has been accomplished by tip cuttings, including the removal and rooting of terminal shoots of three or more leaves, and other methods of propagation have been resorted to such as single eye cuttings, air layering and the use of plunged cane length cuttings, all of which have been successfully used, and indicated that the instant variety will come true to form even under these different kinds of methods.

My new variety is distinctively different from "Burgundy" or any other Philodendron presently known to me.

While the new variety may be compared and/or contrasted with the variety of Philodendron plant disclosed in U.S. Plant Pat. No. 3,034, issued to me, the general differences reside in the substantially greater impression of glossy bronze red and contrasting color of leaves.

My new variety is highly resistant to bacterial soft rot, a disease very prevalent in the Florida and Gulf Coast areas. It is also resistant, in fact virtually immune to the so-called "shot-gun" fungus which is a rather common dehydration problem.

My new variety brings to the trade brilliant colors not available before, the leaves themselves being brilliant bronze red and green with stem and petioles of bright red. In addition to this color, the sheath covering of a new leaf is bright red, curls back as the leaf unfolds and remains on the plant for weeks.

In view of the above description, it will be seen that the general impression provided by this plant is of a group of gloss bronze red curls attached to the stem of the plant.

Insofar as I am aware, no flowers of my new variety have ever been observed, and it is known that flowering of this type of Philodendron is rare, if not almost never occurring. Flower initiation and development would require such ideal conditions with plants at full maturity that no real attempt has ever been made to develop the same.

My new variety may be described as a climber, and when plants of eight leaves or more are involved, these plants will require normal staking.

The rate of growth of my new variety may be termed as being medium, and under normal greenhouse conditions a young plant develops in three or four months from a tip cutting. It may require six to eight months to produce a mature plant from the same type of cutting.

My new variety is vigorous, compact and nonbranching. An average plant of five leaves propagated from a tip cutting may attain a height of twelve inches, and a spread of 19 to 20 inches, a five-leaved plant propagated from a single eye cutting will attain a height of 8 inches, with a spread of 12 to 15 inches.

The detailed observations from which the following description is made were taken in my greenhouse in Orlando, Fla. Those skilled in the art, will readily understand that significant variation may occur in accordance with various environmental conditions including temperature, humidity, day length, and available nutrients, but where the conditions are consistent, the plants are consistent and run true to form from generation to generation.

My new variety has been found to retain its distinctive characteristics through successive asexual reproduction.

The accompanying drawing forming a part hereof, discloses a typical plant of my new variety, the colors being as near true as possible with color illustrations of this type. Color references herein are made to Nickerson Color Fan, published by Munsell Color Company, with observations being recorded by daylight illumination under vinyl of not more than 30% shade.

Comparison and/or contrast may be readily made with the variety of my patented Philodendron plant disclosed in U.S. Plant Pat. No. 3,034 dated Mar. 2, 1971, the general differences residing in the substantially greater impression of glossy bronze red and contrasting colors of leaves.

Form Characteristics

Leaf Shape:
*Mature.*—Ovate.
*Immature.*—Ovate.
*Tip.*—Acute.
*Base.*—Mature — auriculate. Immature — obtuse to cordate.
*Displacement.*—Smooth.
*Margin.*—Entire.
*Veinsation.*—Raised midrib; sunken veins.
Leaf attachment: Stalked.
Leaf arrangement: Alternate.
Petiole: Medium to short.
Stem: Short to 2".
Overall appearance: Dense.

Size Characteristics of Typical Commercial Size

Leaf itself:
*Width—widest point.*—4" to 7".
*Width—1"from tip.*—1½".
*Length.*—6 to 10½".
Petiole: 12".
*Length.*—12".
*Diameter (center).*—½".
*Internode spacing.*—1" to 2".
Stem diameter: ⅜" to ¾".

Color Characteristics

Leaf (top six to seven leaves):
*Top.*—5GY 3/2.
*Bottom.*—2.5R 7/8.
*Margin.*—2.5R 3/7.
Leaf (old bottom leaves):
*Top.*—7.5GY 4/4.
*Bottom.*—2.5GY 4/3.
*Overlay.*—2.5R 7/8.
*Margin.*—2.5R 3/7.
Leaf Veination:
*Midrib.*—2.5R 3/7.
*Veins.*—2.5R 3/7.
Stem: 2.5R 3/7.
Petiole: 2.5R 3/7.
Bracts: 2.5R 4/10 to 2.5R 3/7.

I claim:

1. A new and distinct variety of Philodendron plant substantially as herein disclosed, characterized as to novelty by its superior growth, resistance to shot-gun fungus and bacterial soft rot, glossy bronze red and green color contrasts in immature and mature leaves, the hastate shape of the leaves, the glossy bronze red color of the sheath covering with its tendency to curl back and hang on to the stem for long periods of time.

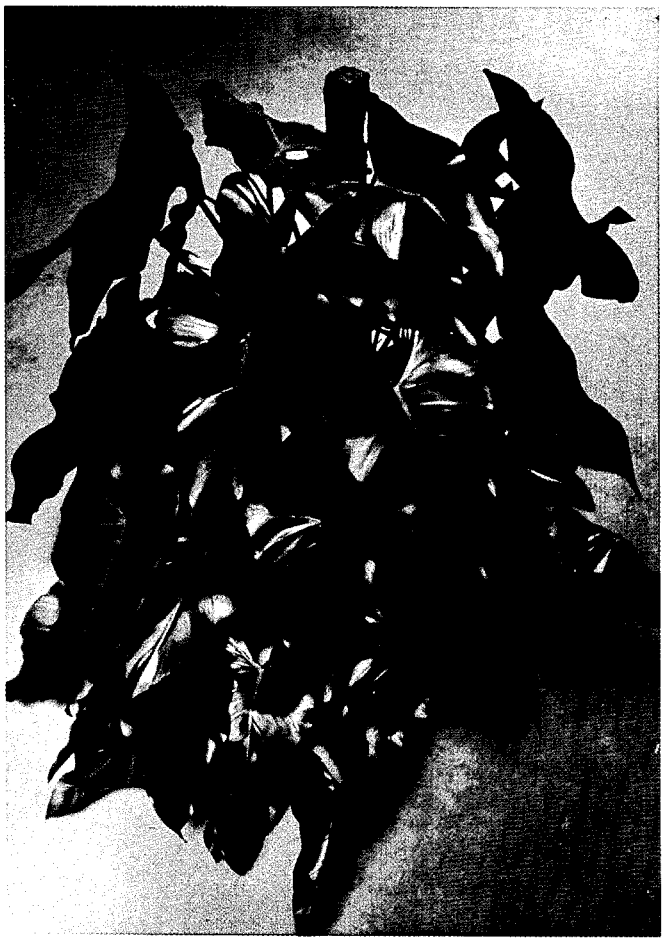

* * * * *